(12) United States Patent
Schmid

(10) Patent No.: US 6,402,964 B1
(45) Date of Patent: Jun. 11, 2002

(54) STERILIZING DEVICE FOR A MEDIUM, PREFERABLY WATER

(75) Inventor: August Schmid, Schwerzenbach (CH)

(73) Assignee: August Schmid-Stiftung Zurich, Zurich (CH)

( * ) Notice: Subject to any disclaimer, the term of this patent is extended or adjusted under 35 U.S.C. 154(b) by 0 days.

(21) Appl. No.: 09/446,948

(22) PCT Filed: Jul. 3, 1998

(86) PCT No.: PCT/CH98/00292
§ 371 (c)(1),
(2), (4) Date: Apr. 14, 2000

(87) PCT Pub. No.: WO99/01381
PCT Pub. Date: Jan. 14, 1999

(30) Foreign Application Priority Data

Jul. 3, 1997 (CH) .............................................. 1625/97

(51) Int. Cl.$^7$ .............................. B01J 19/12; C02F 1/32
(52) U.S. Cl. .................... 210/748; 422/186.3; 250/432; 250/435
(58) Field of Search ................................ 210/748, 232; 422/24, 186.3; 250/432, 436, 435

(56) References Cited

U.S. PATENT DOCUMENTS

| | | | |
|---|---|---|---|
| 4,017,735 A | * | 4/1977 | Siegel |
| 4,274,970 A | * | 6/1981 | Beitzel |
| 4,534,282 A | | 8/1985 | Marinoza |
| 4,623,467 A | | 11/1986 | Hamlin |
| 5,116,582 A | * | 5/1992 | Cooper et al. |
| 5,290,439 A | | 3/1994 | Buchwald |
| 5,320,749 A | * | 6/1994 | Mullen |
| 5,675,153 A | * | 10/1997 | Snowball |
| 5,843,309 A | * | 12/1998 | Mancil |

FOREIGN PATENT DOCUMENTS

| | | |
|---|---|---|
| CH | 298 686 | 7/1954 |
| DE | 93 03 682 | 5/1993 |
| EP | 0 003 879 | 9/1979 |
| EP | 0 202 820 | 11/1986 |
| GB | 498 282 | 2/1939 |
| GB | 1 212 633 | 11/1970 |
| NL | 8 205 084 | 7/1984 |

* cited by examiner

Primary Examiner—David A. Simmons
Assistant Examiner—Fred Prince
(74) Attorney, Agent, or Firm—Wenderoth, Lind & Ponack, L.L.P.

(57) ABSTRACT

The invention relates to a device (50) for sterilizing a medium preferably water. The device has a conduit of pipes (51) through which the medium that is to be purified is passed. At least one removable UV lamp producing ultraviolet radiation is fitted almost concentrically in the conduit. The conduit (51) is U-shaped and has two separate adjacent pipe sections (54). Two sleeves (53), (52) are connected to the inlet and outlet sides of each of these pipe sections, respectively. One of the sleeves (53) forms a channel from one pipe section (54) and the other sleeve (52) forms an inlet and outlet for the medium. This latter sleeve has two flange sections (62), each receiving a UV lamp (55) that extends into a separate one of the pipe sections (54). This results in a sterilizing device which is inexpensive to produce and easy to dissemble for cleaning.

12 Claims, 4 Drawing Sheets

STERILIZING DEVICE FOR A MEDIUM, PREFERABLY WATER

BACKGROUND OF THE INVENTION

The invention relates to a sterilizing device for the sterilizing of a medium, preferably water, with a conduit of pipes through which the medium to be purified passes, with at least one removable UV lamp producing ultraviolet radiation fitted almost concentrically within the conduit.

In a device of this type in accordance with patent specification CH-PS 477 825 a vertically positioned pipe section is provided, the top final section of which is curved around 90° while a pipe bend is connected at its lower end. Furthermore, at this top final section a pipe-connecting piece is positioned, on which a bar-shaped quartz lamp producing ultraviolet radiation is held, which extends into the interior of the pipe. This lamp positioned coaxial with the pipe section achieves the required sterilization by radiating the medium flowing between the lamp and the pipe jacket. For improved radiation spaced-out guide vanes are fixed in the axial direction on the inner wall of the pipe section, which confer turbulence to the medium flowing through the device.

A further well-known apparatus for the sterilization of water in accordance with U.S. Pat. No. 4,623,467 comprises a central sleeve, on the two sides of which there is a connectable connecting sleeve with, in each instance, a radially positioned pipe connecting piece, on both sides of which there is a locking cap and a UV lamp extending through it, which is held at each of its two ends by a respective locking cap. The disadvantage of this apparatus is its relatively expensive manufacture and assembly, in particular because, at each of transition points of various parts connected together, sealings have to be produced so they permanently withstand the corresponding pressures of the water flowing through the apparatus. A further disadvantage is that dead zones of the water flowing through the apparatus form between connecting sleeves and locking covers, in which sterilization is not optimum.

In a known device in accordance with patent application NL-A-8 205 084, a longitudinal sleeve is provided, on which a radially projecting flange is also positioned at both ends for connection to a pipe and, in each instance, a locking cap is fixed, which holds an extending UV lamp. In this device as well the flanges on the longitudinal sleeve, which is made of stainless steel, have to be welded in an expensive manufacturing process.

SUMMARY OF THE INVENTION

In contrast, the present invention is based on the problem of producing a sterilizing unit of the type mentioned previously, which is simple and inexpensive to manufacture, permits problem-free and rapid dismantling and assembling for cleaning and, furthermore, achieves improved radiation of the medium flowing through the unit.

The problem has been solved by having fie conduit of pipes exhibit at least one separate pipe section as well as, in each instance, a sleeve attached to the inlet and outlet side of this pipe section, whereby one sleeve is provided with a flange section, which serves for the detachable fixing of a UV lamp, which, in its installed condition, extends at least partially into the separate pipe section.

With this construction of the invention, this sterilizing device can be produced considerably more cost effectively than known devices and can be dismantled and then reassembled in a very simple manner. Since these UV lamps preferably exhibit a length of up to a few hundred millimeters, this separate pipe section can be used as pole material.

In one very advantageous version the pipe conduit has a U shape and the two sleeves connect, in each instance, two separate pipe sections connected in parallel, whereby one sleeve forms a channel from one pipe section to the other, while the other sleeve forms the inlet and outlet for the medium, with the latter sleeve exhibiting two flange sections for receiving UV lamps extending into the separate pipe sections.

In a further version of the invention a protective cap is provided, which can be removed from the pipe conduit and preferably reveals an integrated plug connection when it is detached. The UV lamp in question is positioned in such a manner in the pipe conduit that, following the removal of the protective cap, the UV lamp can be taken out of this pipe conduit for the purpose of cleaning or replacement.

BRIEF DESCRIPTION OF THE DRAWINGS

Example forms of construction of the invention as well as their further advantages are described in greater detail in the following in accordance with the drawings, in which.

DESCRIPTION OF THE PREFERRED EMBODIMENTS

Figure 1:
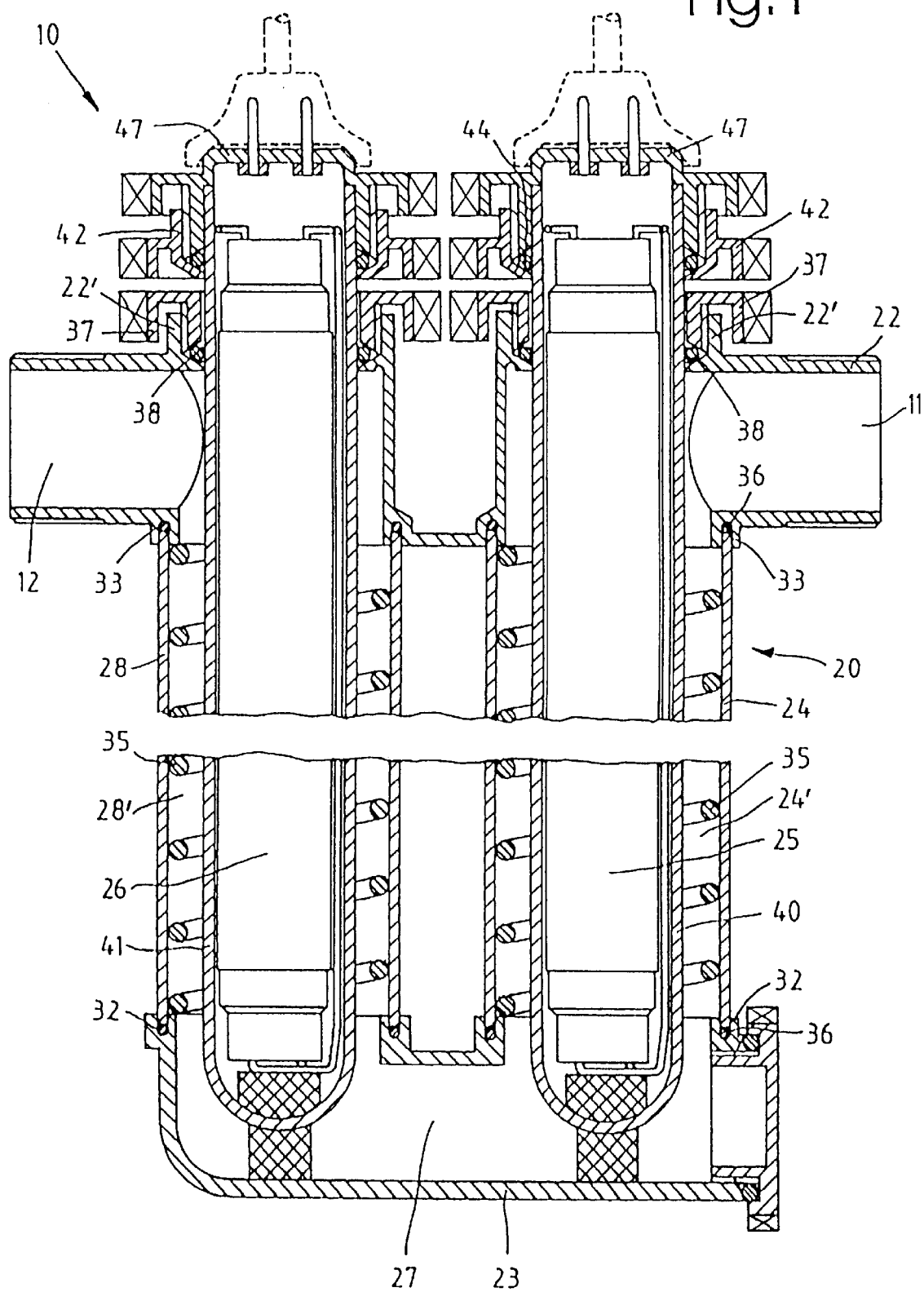
FIG. 1 is a longitudinal sectional view of a sterilization unit of the invention.

FIG. 1 shows a sterilization unit 10 for the sterilization of a medium, preferably water, with a U-shaped pipe conduit 20 through which the medium to be purified passes with two removable UV lamps 25, 26 producing ultraviolet radiation positioned almost concentrically in the conduit 20. Such UV lamps are available on the market and for this reason are not described in greater detail in the following.

In accordance with the invention the pipe conduit exhibits two separate pipe sections 24, 28 as well as two sleeves 22, 23 attached, respectively, to the inlet and outlet side of this pipe sections 24, 28, whereby the one sleeve 22 is provided with a flange section 22' for the detachable fixing of the UV lamps 25, 26, which, in their installed state, extend at least partially into the separate pipe sections 24, 28.

In the present example form of construction the pipe conduit 20 has a U shape, as already mentioned above, and the two sleeves 22, 23 each connect two separate pipe sections 24, 28 arranged in parallel, whereby the one sleeve 22 forms the inlet and outlet 11, 12 while the other sleeve 23 forms the channel 27 of the medium from one to the other of the pipe sections 24, 28. The sleeve 22 forming the inlet and outlet has two flange sections 22', which serve, in each instance, for receiving UV lamps 25, 26.

In the separate pipe sections 24, 28 in question, a device is positioned for the production of turbulence in the medium flowing through the pipe sections between interior walls of the pipe sections 24, 28 and the UV lamps 25, 26. This device is formed as at least one spiral spring 35 wound spirally or otherwise, inserted in the separate pipe section, which, in a pre-stressed state, is located in its axial direction between the two sleeves 22, 23. In this way a very effective and extremely cost effective element has been created for this required improvement in the radiation of the medium flowing through the sterilization unit.

The two separate pipe sections 24, 28 extend, in each instance, in the final section, into an annular tee-slot 32, 33 of the two sleeves 22, 23, which are preferably held together on the outer side by, for example, four connecting rods offset at an angle of 90°. These rods preferably proceed parallel to the pipe sections 24, 28. The latter are advantageously pressed, on the front side, against circumferential sealings 36, which are inserted in this annular tee-slot 32, 33, for the purpose of attaining a perfect seal.

The UV lamps 25, 26 each consist of a lamp tube and a protective sleeve 40, 41 enveloping the lamp tube, which, for example, is made of quartz glass. On the topside a plug section 47 is fixed on this protective sleeve 40, 41 in a detachable manner, with a tightening nut 42. The plug section 47 lies on the protective sleeve 40, 41 and an annular seal 44 between the plug section and the tightening nut 42 achieves the necessary sealing.

The UV lamps 25, 26 each extend coaxially through the pipe sections 24, 28 to the lower sleeve 23 forming a ring slot 24', 28' which let the medium through. In the respective flange section 22' a tightening nut 37 is fixed by means of a thread or the like, which, at the front side, presses an annular seal 38 against the protective sleeve 40, 41 and perfect sealing is effected at this point as well.

With this arrangement of the sterilization unit 10, rapid assembly or dismantling is facilitated for the cleaning or replacement of tie UV lamps.

For the two separate pipe sections 24, 28, aluminum is preferably used, which is anodized, at least on its inner side. This reflects the UV radiation emerging through the protective sleeves 40, 41, whereby maximum radiation of the medium is achieved. As a result of the use of anodized aluminum, these pipe sections can be cut to size from semi-manufactured products in an economical form.

Such a sterilizing unit 10 is particularly suitable for the sterilizing of water from a swimming pool. The water is brought from the pool by a pump or the like, passed through this sterilizing unit 10 with operating UV lamps 25, 26 and then supplied bask to the pool. As a consequence absolutely no additives such as chlorine or the like are required. Within the framework of the invention the sterilizing unit can also be used for other applications. In principle, any liquid or even a gas can be used as the medium.

Obviously the sleeves could also be formed in two or more parts. In particular those with the inlet and outlet could be made of two identically formed sleeves. Furthermore, the flange sections for receiving the UV lamps could also be assigned to the sleeve 23.

Figure 2:
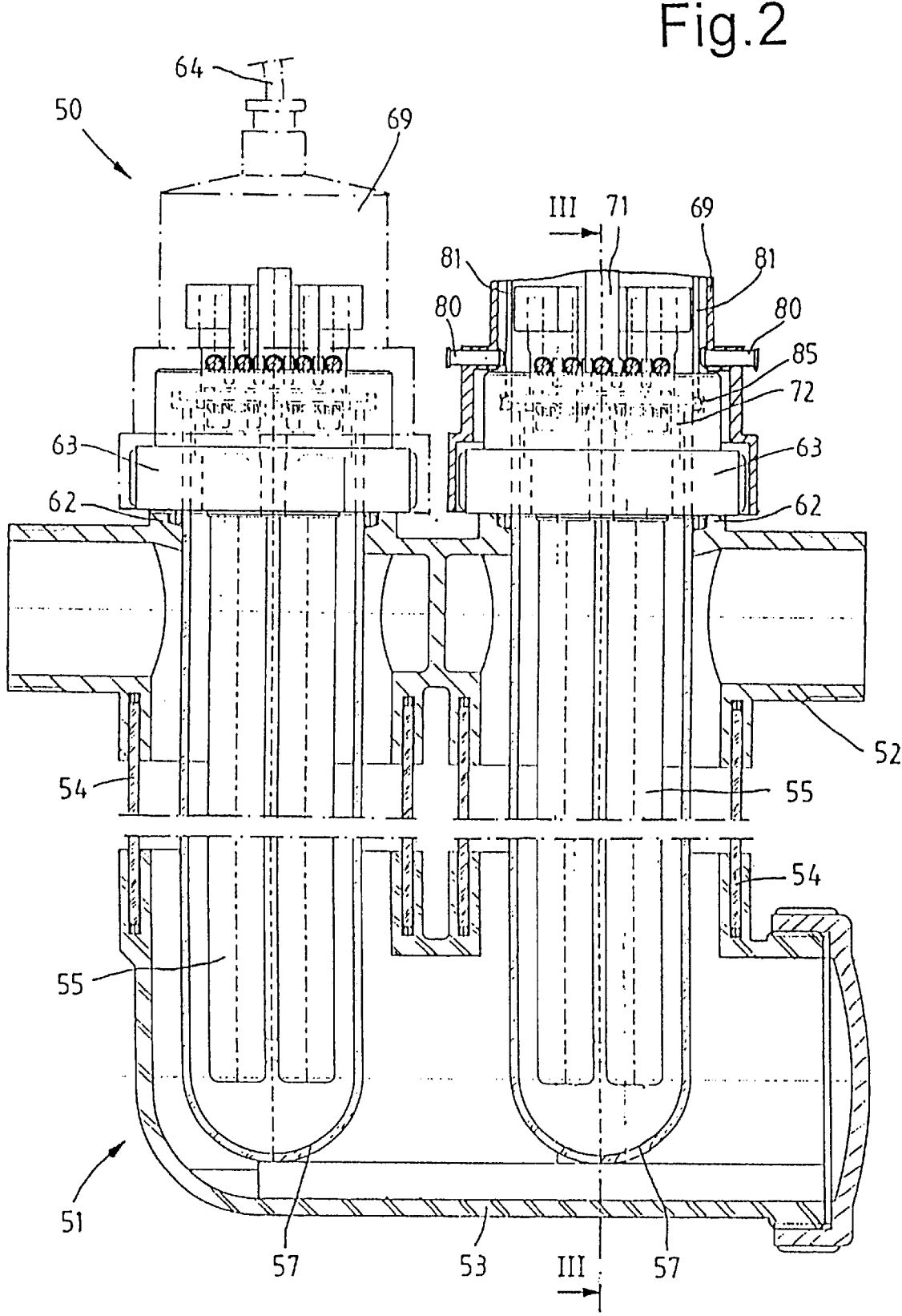
FIG. 2 is a longitudinal sectional view of a variation of a sterilization unit of the invention.
Figure 3:
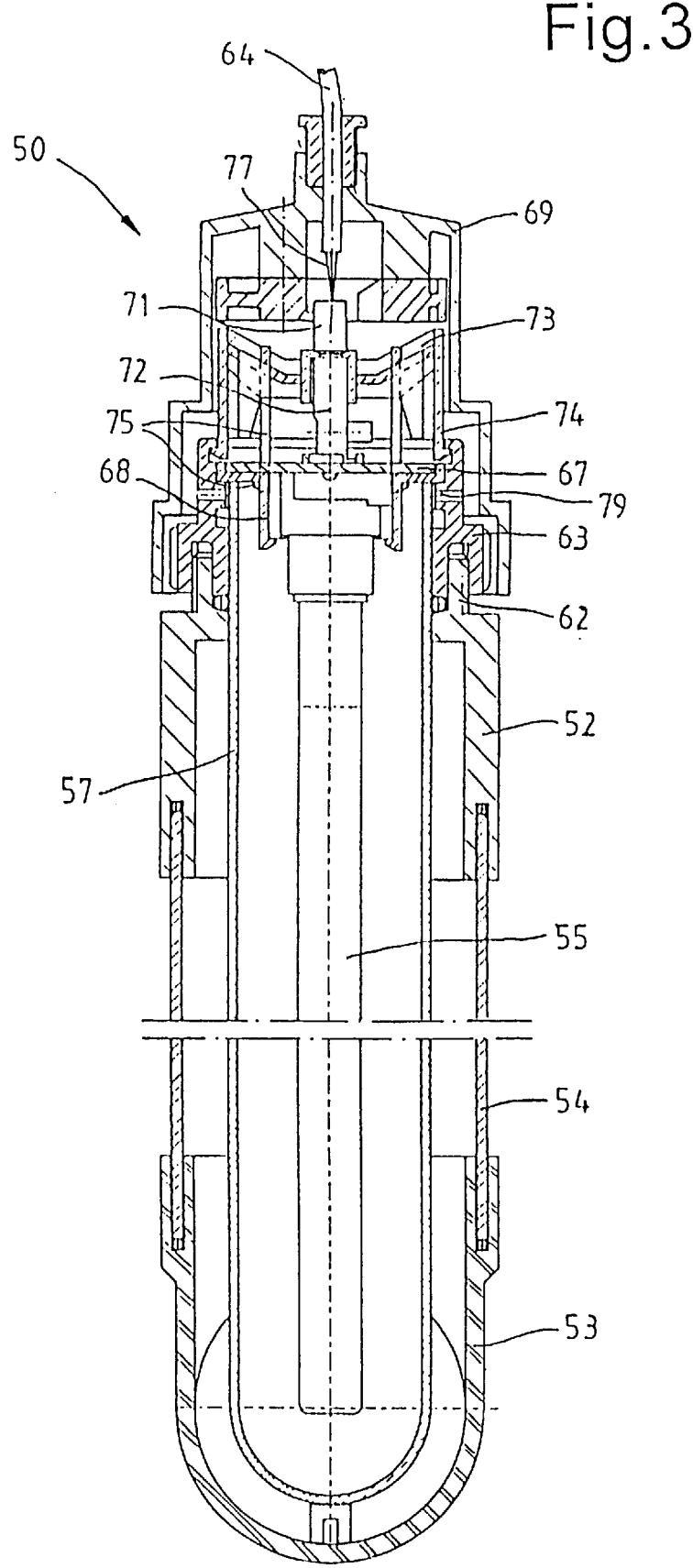
FIG. 3 is a cross-sectional view taken through the sterilization unit along the line III—III in accordance with FIG. 2.

FIGS. 2 and 3 show a further very advantageous form of construction of a sterilizing unit 50 of the invention, which is also formed of a U-shaped pipe conduit 51 and, in each instance, a UV lamp 55 is integrated in the two sides of this conduit 51 and arranged in parallel. These UV lamps 55 are, in each instance, formed of two tubes positioned in parallel in the normal manner.

In accordance with the invention, the U shaped pipe conduit 51 exhibits two separate pipe sections 54 as well as, in each instance, sleeves 52, 53 attached to the pipe sections 54 on the inlet and outlet side, whereby the one sleeve 52 is provided, in each instance, with a flange section 62 for the two pipe sections 54, which serve for the detachable fixing of the UV lamps 55 extending, in an installed state, through the separate pipe sections 54 in each instance. The two sleeves 52, 53 are held together on the outside by connecting poles located in parallel to the pipe sections and not shown in greater detail, whereby preferably four of these connecting poles are provided.

In accordance with FIG. 3 the UV lamp 55 is held on the flange section 62 of the sleeve 52 located on the topside of the unit 50. The UV lamp 55 used in a protective sleeve 57 is connected by a plug connection and a cable 64 to the main supply (220V). This plug connection consists of a plug section 71 fixed in a protective cap 69 with five downwardly extending pins and a socket 72 located directly above the UV lamp 55. The latter as well as the plug section 71 and the UV lamp are commercially available and thus contribute to the cost-effective production of the unit 50. The socket 72 with five connector sockets arranged in parallel and accessible from above is held in a supporting element 73, which is connected with and can be detached from an attachment sleeve 63 on the flange section 62 by means of a snap closure 74. The plug section 71 is, for its put, fixed in the protective cap 69, which, in its mounted state, serves to cover the plug connection. Wire connections 77 lead into the plug section 71 and these are connected to the power supply by means of the cable 64 contained in the protective cap 69.

On the underside of the supporting element 73 a disk 67 is held by means of a snap closure 75, which, for its put, is provided with a hook closure 68 holding the UV lamp. This disk 67 is inserted in the attachment sleeve 63 and lies virtually on top of the protective sleeve 57 so that the interior is closed by the latter during operation.

For the removal of the protective cap 69 two push buttons 80 are positioned opposite each other in an adjustable manner on the side in the protective cap 69, and on the inner side flexible locking catches 81 of a snap closure 85 are present, whereby the latter moreover is formed by corresponding grooves on the attachment sleeve 63. The push buttons 80 can be activated by hand pressure and, as a result, the locking catches 81 are bent inwardly, as a result of which the protective cap 69 is released and can be raised up. At the same time the plug section 71 is removed from the socket 72 and thus there is no further current in the lamp and in the unit.

After the removal of the protective cap 69, the UV lamp 55 can be dismantled and cleaned. To this end the snap closure 74 made accessible from the outside, and the supporting element 73 is disengaged and the UV lamp 55 can be taken out together with the socket 72 as a complete unit. Subsequently the protective sleeve 57 can be taken out after the attachment sleeve has been screwed off. These and also the inner wall of the pipe section 54 can then be cleaned so optimum radiation and/or reflection is guaranteed once again. Afterwards the protective sleeve 57, the sleeve 63, the UV lamp and the protective cap 69 can be assembled again without any tool being required. Thus, this unit can be taken apart and returned to an operational state in a very simple manner within a few minutes.

In the event of a defect, the UV lamp 55 can also be replaced within a very short period. To this end after the removal of the protective cap 69, once again the snap closure 74 on the supporting element 73 is disengaged and the UV lamp 55 together with the socket 72 can be removed as a complete unit. By loosening the hooks 68 as well as the cable connecting the lamp 55 with the socket 72, this lamp 55 can be replaced.

Furthermore, in the attachment sleeve 63, a discharge aperture 79 is also provided, through which the leakage water penetrating from the pipe circuit 51 between the protective sleeve 57 and the attachment sleeve 63 surrounding the protective sleeve 57 can flow away.

Figure 4:
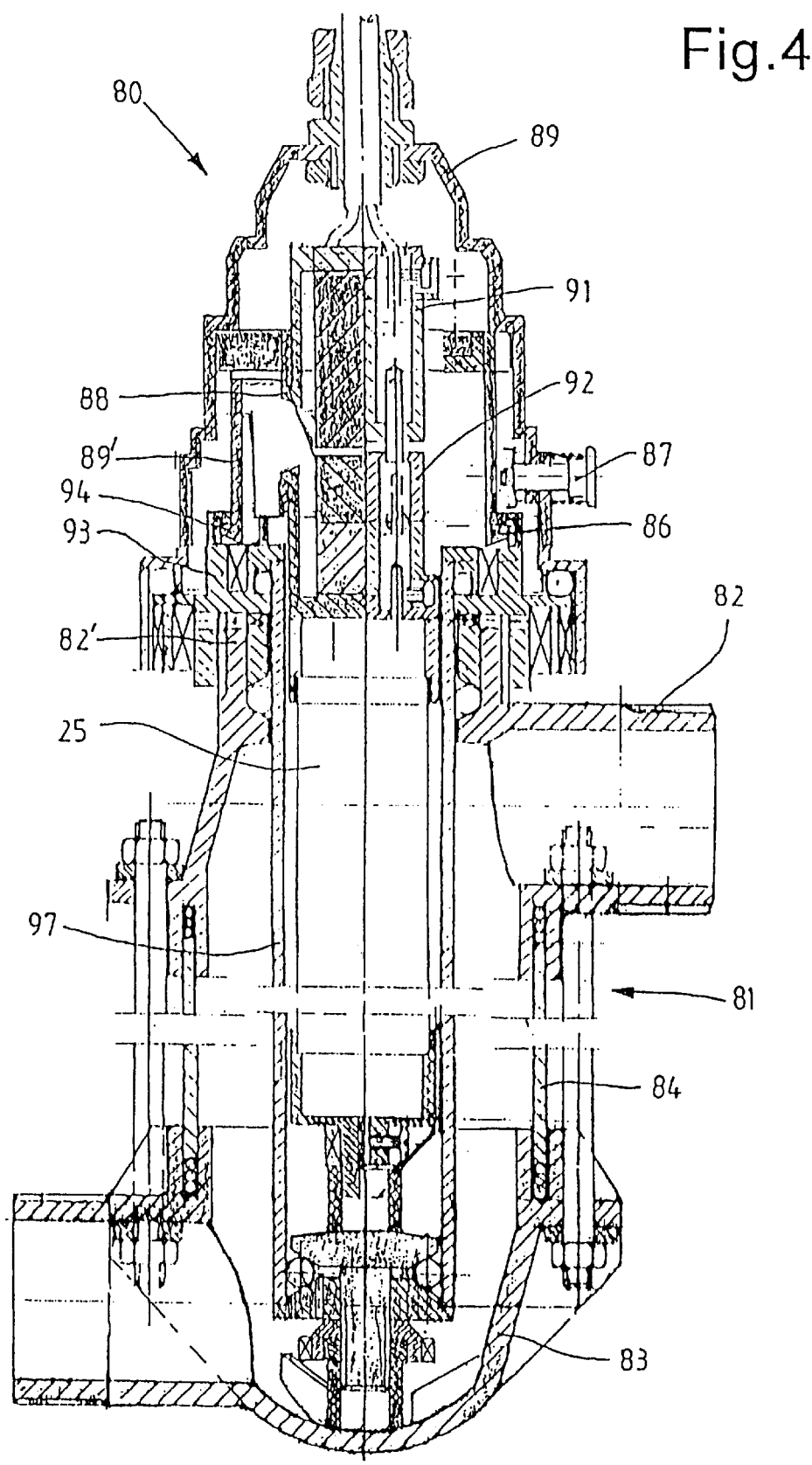
FIG. 4 is a further longitudinal sectional view of another variation of a sterilization unit of the invention.

FIG. 4 shows a sterilizing unit 80, which, in itself, has the same construction as the unit in accordance with FIG. 3 and for this reason only the differences are explained in greater detail in the following. This unit 80 exhibits a pipe conduit 81, which once again consists of an inlet-side and outlet-side sleeve 82, 83 as well as a pipe 84 extending between these sleeves 82, 83. A UV lamp 25 tightly enclosed in a protective sleeve 97 is connected to the main supply by means of a plug connection of a different nature than that shown in FIG. 3 and centred at its lower end by means of a seal in the sleeve 82. This plug connection is a four pole plug connection and consists of a plug section 91 fixed in a protective cap 89 and a socket 92 located at the lower side of the cap 89, which socket 92 is held by a supporting element 89' above the UV lamp 25, which is connected with and can be detached from an attachment sleeve 93 on a flange section 82' by means of a snap closure 94 or the like.

In the right half of the longitudinal section of the plug connection as well as of the protective cap 89, a snap closure 86 or the like is shown, which is released by a spring-loaded push button 87 and releases the protective cap 89 together with the plug section 91 from the flange section 82' of the sleeve 82. In contrast, in the released state of this snap closure 86, the attachment sleeve 93 and the UV lamp 25 are connected with the protective cap 89.

In the left half of the longitudinal section of the plug connection as well as of the protective cap 89, which is shown offset by 90° to the right-half, it is apparent that, for its part, the plug section 91 is held in the protective cap 89 by means of a snap closure 88 or the like, which, in a assembled state, serves as a cover for the plug connection.

In principle, the UV lamp could also be attached directly to the protective cap. During removal, therefore, the protective cap would be taken off together with the UV lamp.

What is claimed is:

1. An apparatus for sterilizing a medium, comprising;
   a conduit through which a medium is to be passed, said conduit including
   (i) a first conduit section,
   (ii) a first sleeve in fluid communication with an inlet of said first conduit section, said first sleeve including a first flange section, and
   (iii) a second sleeve in fluid communication with an outlet of said first conduit section; and
   a first UV lamp for producing ultraviolet radiation, said first UV lamp being removably connectable to said first flange section such that when said UV lamp is connected to said first flange section said UV lamp extends at least partially within said first conduit section in a substantially concentrical manner.

2. The apparatus according to claim 1, wherein said conduit has a U-shaped configuration and further includes
   (iv) a second conduit section that is parallel with said first conduit section, wherein said second sleeve defines a channel that places said first conduit section in fluid communication with said second conduit section, said first sleeve is also in fluid communication with an outlet of said second conduit section, and said first sleeve also includes a second flange section that is to have removably connected thereto a second UV lamp which extends into said second conduit section when the second UV lamp is connected to said second flange section.

3. The apparatus according to claim 2, further comprising a wound wire within each of said first conduit section and said second conduit section for producing turbulence within the medium as the medium flows through said first conduit section between an interior wall of said first conduit section and said first UV lamp when said first UV lamp is extending into said first conduit section, and for producing turbulence within the medium as the medium flows through said second conduit section between an interior wall of said second conduit section and the second UV lamp when the second UV lamp is extending into said second conduit section.

4. The apparatus according to claim 2, wherein said first conduit section and said second conduit section each include on an interior wall thereof a material that is capable of reflecting UV radiation.

5. The apparatus according to claim 4, further comprising a wound wire within each of said first conduit section and said second conduit section for producing turbulence within the medium as the medium flows through said first conduit section between the interior wall of said first conduit section and said first UV lamp when said first UV lamp is extending into said first conduit section, and for producing turbulence within the medium as the medium flows through said second conduit section between the interior wall of said second conduit section and the second UV lamp when the second UV lamp is extending into said second conduit section.

6. The apparatus according to claim 4, wherein said material comprises anodized aluminum.

7. The apparatus according to claim 6, further comprising a wound wire within each of said first conduit section and said second conduit section for producing turbulence within the medium as the medium flows through said first conduit section between the interior wall of said first conduit section and said first UV lamp when said first UV lamp is extending into said first conduit section, and for producing turbulence within the medium as the medium flows through said second conduit section between the interior wall of said second conduit section and the second UV lamp when the second UV lamp is extending into said second conduit section.

8. The apparatus according to claim 1, wherein said first conduit section includes on an interior wall thereof a material that is capable of reflecting UV radiation.

9. The apparatus according to claim 8, further comprising a wound wire within said first conduit section for producing turbulence within the medium as the medium flows through said first conduit section between the interior wall of said first conduit section and said first UV lamp when said first UV lamp is extending into said first conduit section.

10. The apparatus according to claim 8, wherein said material comprises anodized aluminum.

11. The apparatus according to claim 10, further comprising a wound wire within said first conduit section for producing turbulence within the medium as the medium flows through said first conduit section between the interior wall of said first conduit section and said first UV lamp when said first UV lamp is extending into said first conduit section.

12. The apparatus according to claim 1, further comprising a wound wire within said first conduit section for producing turbulence within the medium as the medium flows through said first conduit section between an interior wall of said first conduit section and said first UV lamp when said first UV lamp is extending into said first conduit section.

* * * * *